United States Patent
Rosen et al.

(10) Patent No.: US 7,521,249 B2
(45) Date of Patent: Apr. 21, 2009

(54) METHOD AND COMPOSITION FOR THE PREPARATION OF A SAMPLE FOR ANALYSIS

(75) Inventors: Jacob Rosen, Scotch Plains, NJ (US); Gregory Shmuylovich, Springfield, NJ (US)

(73) Assignee: L'Oreal, Paris (FR)

( * ) Notice: Subject to any disclaimer, the term of this patent is extended or adjusted under 35 U.S.C. 154(b) by 834 days.

(21) Appl. No.: 11/004,870

(22) Filed: Dec. 7, 2004

(65) Prior Publication Data

US 2005/0170518 A1     Aug. 4, 2005

Related U.S. Application Data

(60) Provisional application No. 60/528,712, filed on Dec. 12, 2003.

(51) Int. Cl.
*G01N 33/20*     (2006.01)
(52) U.S. Cl. .................. 436/83; 436/2; 436/6; 436/22; 436/23; 436/24; 436/73; 436/80; 436/81; 436/82; 436/84; 436/171; 436/173; 436/175; 510/247; 510/253; 510/254; 510/257
(58) Field of Classification Search .................. 422/61; 436/2, 6, 20–22, 60, 73, 80–84, 155, 171, 436/173, 175; 510/247, 253–254, 257
See application file for complete search history.

(56) References Cited

U.S. PATENT DOCUMENTS

| 4,444,628 | A | * | 4/1984 | Furukawa et al. | ........... 205/202 |
| 5,417,819 | A | * | 5/1995 | Askin et al. | ................. 428/687 |
| 5,616,231 | A | * | 4/1997 | Askin et al. | ................. 205/153 |
| 6,194,365 | B1 | * | 2/2001 | Lee | ............................. 510/175 |
| 7,153,434 | B1 | * | 12/2006 | Dennis | ........................ 210/670 |

FOREIGN PATENT DOCUMENTS

| JP | 7-185797 | * | 7/1995 |
| SU | 881158 | * | 11/1981 |
| SU | 1346699 | * | 10/1987 |

\* cited by examiner

*Primary Examiner*—Arlen Soderquist
(74) *Attorney, Agent, or Firm*—Oblon, Spivak, McClelland, Maier & Neustadt, P.C.

(57) ABSTRACT

The present invention relates to the preparation of a sample. Preferably, the sample is a sample to be analyzed, for example for ingredient content, etc. Preferred samples include foods, cosmetics, paints, coatings, adhesives, tanning agents, fabrics, chemical compositions, dyestuffs, samples subject to forensic studies, etc. Samples prepared according to the invention method are digested in sulfuric acid, nitric acid, and one or more fluoride salts selected from LiF, NaF, RbF, CsF and KF and then preferably subjected to analysis for metal content, etc, for example using atomic absorption ("AA") and inductively coupled plasma ("ICP").

13 Claims, No Drawings

METHOD AND COMPOSITION FOR THE PREPARATION OF A SAMPLE FOR ANALYSIS

FIELD OF THE INVENTION

The present invention relates in part to the preparation of a sample. Preferably, the sample is a sample to be analyzed, for example for ingredient content, etc. Preferred samples include foods, cosmetics, paints, coatings, adhesives, tanning agents, fabrics, chemicals, compositions, samples subject to forensic studies, drugs, sediments, etc. Samples prepared according to the invention method are preferably subjected to analysis for metal content, etc, for example using atomic absorption ("AA") and/or inductively coupled plasma ("ICP"). The sample prepared according to the invention also makes up a part thereof, as does the method of analysis of such a sample, and the sample prepared and analyzed. In addition, the invention also includes various reagent combinations useful for accomplishing the invention method, such as a pre-made digestion mixture composition, a modifier composition, etc. Kits containing reagents and/or digestion vessel(s) useful for accomplishing the invention method also make up a part of the invention.

Additional advantages and other features of the present invention will be set forth in part in the description that follows and in part will become apparent to those having ordinary skill in the art upon examination of the following or may be learned from the practice of the present invention. The advantages of the present invention may be realized and obtained as particularly pointed out in the appended claims. As will be realized, the present invention is capable of other and different embodiments, and its several details are capable of modifications in various obvious respects, all without departing from the present invention. The description is to be regarded as illustrative in nature, and not as restrictive.

BACKGROUND OF THE INVENTION

Methods for preparing samples for analysis generally rely on dangerous chemical reagents, hazardous conditions, and long preparation times. The United States Pharmacopoeia (USP) method for $TiO_2$ determination requires digesting a sample with boiling $H_2SO_4$ for 8 hours with subsequent filtration of the solution. This procedure is dangerous, lengthy and not sufficiently accurate because a filtration step is involved. While a cosmetic formulation containing $TiO_2$ could be treated in a microwave with a mixture of nitric acid and HF to produce a clear solution suitable for Ti determination by AA, HF is a very strong health hazard, and during digestion high pressures, for example up to 450 psi, may develop. Thus, in addition to being hazardous to use, the accuracy of these methods and time they take to complete make them less than desirable.

DETAILED DESCRIPTION OF THE PREFERRED EMBODIMENTS

The present invention provides a sample preparation method that is especially useful in preparing samples for subsequent analysis, and preferably for the determination of the metal content in the sample, for example by AA and/or ICP. In a highly preferred embodiment the sample is a cosmetic sample, possibly containing silica. The determination of the titanium content of such samples makes up a highly preferred embodiment of the invention.

Generally, sample preparation according to the invention can be accomplished by combining the sample with the following reagents: sulfuric acid, nitric acid, and one or more fluoride salts selected from the group consisting of highly soluble fluoride salts such as LiF, NaF, KF, RbF, and CsF. More preferably LiF, NaF, KF. The combination is then heated, for example in a microwave. Preferably, the sulfuric acid used is 95-98% $H_2SO_4$ and the nitric acid used is 70% $HNO_3$.

The method and manner by which the sample and reagents are combined, and the order in which they are combined, is not limited and includes all orders of mixing and addition, etc. One convenient methodology is to use a pre-made digestion mixture composition comprising the sulfuric acid, nitric acid, and one or more fluoride salts, and to combine this pre-made composition and the sample before heating. The invention procedure is highly suitable for dissolution of samples containing one or more of Li, Na, K, Rb, Cs, Al, Ga, In, Ti, Ti, V, Cr, Mn, Fe, Co, Ni, Cu, and Zn.

As a rule of thumb, the invention digestion mixture composition can generally comprise, from a practical viewpoint and using about 0.03-0.40 grams of sample, 10-20 ml of 95-98% $H_2SO_4$, 1-3 ml of 70% $HNO_3$, and 0.2-2.0 g of fluoride-containing salt. Generally, the volume ratio of $H_2SO_4$ to $HNO_3$ (i.e., $H_2SO_4/HNO_3$ vol/vol) is preferably about 5-10+, preferably 6-10, more preferably 7-9, these ranges specifically including all values and subranges therebetween. For this ratio the higher values tend to work better, meaning that they are more accurate and useful, particularly in a standardized and repetitive setting where numerous samples are to be analyzed. Preferably, the total amount of fluoride salt is greater than or equal to 0.2 g per 11 ml of $H_2SO_4/HNO_3$, more preferably greater than or equal to 0.25, 0.5, 0.8, etc. g. A practical upper limit on total fluoride salt is about 0.30 g per 11 ml of $H_2SO_4/NO_3$. Generally, about 11.5 ml of digestion reagents $H_2SO_4$ and $HNO_3$ and 0.25 g of fluoride salt are used to digest, or prepare a 0.20-0.30 g sample by heating. Weights and volumes of $H_2SO_4$ and $HNO_3$ were selected based on the 100 ml digestion vessels and could be adjusted proportionally for the different digestion vessels.

The invention method can be supplemented by the addition, after the heating of the sample/digestion mixture composition, of a modifier to the sample/digestion mixture in order to increase the accuracy of the method. For example, the modifier can increase instrumental absorbance readings and minimize possible interference. This modifier is generally a composition comprising aluminum nitrate, sodium chloride, phosphoric acid and water, and this modifier can be prepared as a pre-made additive composition or the components can be added in any order to the heated sample/digestion mixture composition. Such addition preferably takes place after the heated mixture has cooled, for example to below 30 C°.

The modifier generally comprises about 50-90 g aluminium nitrate, about 5-15 g sodium chloride, about 150-250 ml phosphoric acid and about 750 ml water. A preferred pre-made additive composition can be prepared by the following method:
1. Weigh 69 g of aluminum nitrate and 8.5 g of sodium chloride in a 1000 ml glass beaker. Add about 500 mL of deionized water and mix well to dissolve.
2. Slowly add 200 mL of Phosphoric Acid, mix and cool to room temperature.
3. Transfer the solution into a 1000 mL volumetric flask, dilute to volume with deionized water and mix.

The modifier can be added in amounts of about 0.5-1.5 ml per 10 ml of sample/digestion mixture composition, preferably 1.0 etc, ml. A preferred modifier described in this invention was designed for titanium analysis by AAS (atomic adsorption spectroscopy). Analysis of other elements may require different modifier composition or no modifier at all.

Heating is preferably accomplished via microwave heating. Preferred heating parameters are shown in Table 3 below.

When conventional heating is used, the sample/digestion mixture composition is generally heated to a temperature of 50-300° C., preferably 125-250° C., most preferably at about 200° C. for from 4-12 hours, preferably 6-9 hours, more preferably about 8 hrs, and preferably allowed to cool. Microwave heating can be accomplished much quicker, for example on the order of 5 min-2 hrs, more preferably less than one hour, for example 20-40 min. Cooling may be done naturally by allowing the heated mixture to rest at room temperature, or by active cooling in a water or ice bath, etc.

While not bound or limited by any theory whatever herein, it is believed that $H_2SO_4$ may serve for metal digestion and oxidation of organics, $HNO_3$ may also serve the same purpose (but it is a stronger oxidizer than sulfuric acid), and the fluoride salt may react with silicon converting it to volatile $H_2SiF_6$ and possibly also forming complex metal fluorides. Alternatively or in addition, the nitric acid may oxidize the organic matter of the sample, the sulfate ions may form soluble complexes with titanium, and the fluoride may bind silica.

The invention method utilizes chemicals that should not contact the skin, and thus the use of gloves is recommended (e.g., NeoPro from Spectrum Inc., Part # 10NOE). When the heating is accomplished via microwave, one useful system is the Multiwave 3000, Microwave Digestion System with temperature and pressure control (Perkin Elmer Corp.). Heavy-duty digestion vessels equipped with a safety disk capable to withstand e.g., 800 psi and 220° C. with such a system.

Preferred reagents useful herein include the following:
1. Aluminum Nitrate, ACS reagent grade, GFC Chemicals #11551, or equivalent.
2. Calcium Hydroxide, ACS reagent grade, J.T. Baker # 1305-62-0, or equivalent.
3. Potassium Fluoride, ACS reagent grade, J.T. Baker #3123-01, or equivalent.
4. Sulfuric Acid (95-98%), ACS reagent grade, EM Science SX 1244-14, or equivalent.
5. Nitric Acid (69.0-70.0%), ACS reagent grade, J.T. Baker # 9601-00, or equivalent.
6. Phosphoric Acid (85%), ACS certified, Fisher Chemicals # A242-500, or equivalent.
7. Sodium Chloride, ACS reagent grade, J.T. Baker # 3624-01, or equivalent.
8. Water, deionized, USP reagent grade.

As noted above, the invention method finds particular use in the field of cosmetics and more particularly in the determination/quantification of components such as metals in cosmetics. Such cosmetics can be in solid, liquid, semi-solid or semi-liquid form, etc, including gels, creams, lotions, pastes, pomades, powders, compacts, sticks, etc.

In a preferred embodiment of the invention method samples are digested by combining them, optionally after physically breaking up the sample, with the digestion reagents and heating as described above. Alternatively or in addition, a sample can be sonicated before or after mixing with the digestion reagents to aid in digestion, particularly for solid and semi-solid samples. Heating generally occurs for 30-35 min in a microwave until the sample appears clear. Then, the sample is quantitatively transferred into a volumetric flask, the modifier is optionally added, the solution is diluted to volume, and the mixture is analyzed, for example for metal content via AA or ICP. One of ordinary skill in the art knows how to subject such a sample to such analysis, and how to calibrate and use such instruments in order to achieve accurate and reproducible results for different metals with various limits of quantitation (LOQ).

The reagents used herein can be provided in the form of a kit, which may take the form of individually packaged reagents present in a larger container or package, optionally where the amounts of individual reagents in the kit are pre-measured for use in the invention method.

EXAMPLES

The invention will now be illustrated by the following non-limiting examples. In these examples, the amounts of metals are indicated as percentages by weight.

1. Weigh (to the nearest 0.1 mg) a known amount of sample (Tables 1A and 1B) in a microwave digestion vessel. Use a transfer tube or 1 mL plastic disposable syringe to transfer a sample.
2. Weigh 0.20-0.30 g of potassium fluoride and transfer into a vessel.
3. Add 10 mL of sulfuric acid and 1.5 mL of nitric acid into each vessel in a fume hood.
4. Expand a vessel cap using the tool provided. Cap the vessel, tighten the venting screw and place the vessel into ceramic jacket, following the microwave manual.

Sample Digestion

1. Load the vessels in the rotor in a symmetrical pattern to ensure the uniformity of temperature and pressure distribution during the digestion. The venting screws should be pointing outward. ALWAYS RUN TWO OR MORE VESSELS.
2. After placing vessels into the rotor, finger-tight knurled nuts.
3. Cover the rotor with the lid and lock it.
4. Ensure that the oven vent hose exhausts to a fume hood.
5. Run the microwave oven using the conditions shown in Table 2.
6. Allow the vessels to cool to about 30° C. Transfer the rotor to the hood. Make sure that the vents are pointing away from you. Using the tool provided slowly loosen the vent screws to allow gases to escape. Remove the caps.

Sample Dilution

1. Add about 20 mL of deionized water, sulfuric acid, if necessary, and matrix modifier to the appropriate volumetric flask* as per Tables 1A and 1B. Quantitatively transfer sample solution from the vessel to the flask.
2. Rinse the vessel and the lid with deionized water not less than three times and transfer the washings to the same flask. Let the flask cool to room temperature.
3. Dilute to volume with deionized water and mix well. This is the Sample Solution. Make additional dilutions if necessary. The final dilution should result in a concentration between 20 µg/mL and 50 µg/mL.

* When the second dilution is necessary, add acid and modifier to the second flask.

TABLE 1A

Sample Preparation Based on Theoretical Concentration of $TiO_2$

| % TiO2** | Flask (mL) | Wt (g) | Sulfuric Acid (mL) | Modifier (mL) |
|---|---|---|---|---|
| 0.8-1.0 | 50 | 0.26-0.30 | 0 | 5.0 |
| 1.1-1.4 | 50 | 0.19-0.24 | 0 | 5.0 |
| 1.5-1.9 | 50 | 0.14-0.18 | 0 | 5.0 |
| 2.0-2.4 | 100 | 0.21-0.28 | 0 | 10.0 |
| 2.5-3.4 | 100 | 0.17-0.20 | 0 | 10.0 |
| 3.5-4.4 | 100 | 0.12-0.15 | 0 | 10.0 |
| 4.5-5.4 | 100 | 0.09-0.12 | 0 | 10.0 |
| 5.5-6.4 | 250 | 0.19-0.26 | 15.0 | 25.0 |
| 6.5-7.4 | 250 | 0.16-0.23 | 15.0 | 25.0 |
| 7.5-8.4 | 250 | 0.14-0.20 | 15.0 | 25.0 |
| 8.5-9.4 | 250 | 0.12-0.18 | 15.0 | 25.0 |
| 9.5-10.4 | 250 | 0.11-0.16 | 15.0 | 25.0 |
| 10.5-11.4 | 250 | 0.10-0.15 | 15.0 | 25.0 |
| 11.5-12.4 | 250 | 0.09-0.13 | 15.0 | 25.0 |
| 12.5-13.4 | 250 | 0.08-0.12 | 15.0 | 25.0 |
| 13.5-14.4 | 250 | 0.08-0.11 | 15.0 | 25.0 |

**For samples with concentration of titanium dioxide less than 2.0% use 20 mL of sulfuric acid and 10 mL of matrix modifier for preparation of standards.

TABLE 1B

Sample Preparation Based on Theoretical Concentration of $TiO_2$

| % TiO2 | Flask 1 (mL) | Aliquot (mL) | Flask 2 (mL) | Wt (g) | Sulfuric Acid (mL) | Modifier (mL) |
|---|---|---|---|---|---|---|
| 14.5-15.4 | 100 | 15 | 100 | 0.19-0.29 | 8.5 | 10.0 |
| 15.5-16.4 | 100 | 15 | 100 | 0.18-0.27 | 8.5 | 10.0 |
| 16.5-17.4 | 100 | 15 | 100 | 0.17-0.26 | 8.5 | 10.0 |
| 17.5-18.4 | 100 | 15 | 100 | 0.16-0.24 | 8.5 | 10.0 |
| 18.5-19.4 | 100 | 15 | 100 | 0.15-0.23 | 8.5 | 10.0 |
| 19.5-20.4 | 100 | 15 | 100 | 0.14-0.22 | 8.5 | 10.0 |
| 20.5-21.4 | 100 | 15 | 100 | 0.14-0.21 | 8.5 | 10.0 |
| 21.5-22.4 | 100 | 15 | 100 | 0.13-0.20 | 8.5 | 10.0 |
| 22.5-23.4 | 100 | 15 | 100 | 0.12-0.19 | 8.5 | 10.0 |
| 23.5-24.4 | 100 | 15 | 100 | 0.12-0.18 | 8.5 | 10.0 |
| 24.5-25.4 | 100 | 15 | 100 | 0.11-0.18 | 8.5 | 10.0 |

TABLE 2

Microwave Oven Heating Program

| | Stage 1 | Stage 2 | Stage 3 |
|---|---|---|---|
| Power, watt | 1200 | 1400 | 0 |
| Ramp, min | 10 | 5 | 0 |
| Hold, min | 5 | 6 | 20 |
| Fan Speed | 1 | 1 | 3 |

Calculations $$\% \text{ TiO}_2 = \text{Conc. Ti} \times \frac{\text{Flask Volume(mL)}}{\text{Sample Weight(g)}} \times DF \times 1.668 \times 10^{-4}$$

Where:

Conc. Ti=measured concentration of Titanium, μg/mL.

$$1.668 \text{(ratio factor)} = \frac{\text{Molecular Weight(TiO}_2)}{\text{Atomic Weight(Ti)}}$$

$10^{-4}$=converts concentration from μg/mL to %

DF (dilution factor)=volume of the Flask 2/Aliquot

Example of Calculation

1. The target concentration of titanium dioxide in the sample is 5.0%. If the actual reading of the instrument is 36.6 μg/mL and the sample weight is 0.1204 g, the measured concentration of titanium dioxide in the sample is:

$$\% \text{ TiO}_2 = 36.6 \times \frac{100}{0.1204} \times 1.668 \times 10^{-4} = 5.07\%$$

2. The target concentration of titanium dioxide in the sample is 18.0%.

If the actual reading of the instrument is 35.6 μg/mL and the sample weight is 0.2204 g, the measured concentration of titanium dioxide in the sample is:

$$\% \text{ TiO}_2 = 35.6 \times \frac{100}{0.2204} \times \frac{100}{15} \times 1.668 \times 10^{-4} = 17.96\%$$

Example 1

Cosmetic Formulation Containing 5% of TiO2 was Analyzed for Titanium Content.

As per Table 1A 0.1028 g of the sample were weighed in a microwave digestion vessel. An 1 mL plastic disposable syringe was used to transfer a sample. 0.2312 g of potassium fluoride were weighed and transferred into a vessel. 10 mL of sulfuric acid and 1.5 mL of nitric acid were added into each vessel in a fume hood. Vessel cap was expanded using the tool provided. Then the vessel was capped, the venting screw tightened and the vessel was placed into ceramic jacket, following the microwave Multiwave 3000 manual.

Sample Digestion

The vessel was placed in the rotor, the rotor was placed into Multiwave 3000 and digestion was conducted using the conditions shown in Table 2. the vessels were allowed to cool to about 30° C. Then the rotor was transfered to the hood. The vent screws were loosen to allow gases to escape and the cap were removed.

Sample Dilution 20 mL of deionized water and 10 mL of matrix modifier were added to 100-mL volumetric flask as per Table 1A. The sample solution was transferred quantitatively from the vessel to the flask. The vessel and the cap were rinsed with deionized water three times and the washings were transferred to the same flask. The flask was cooled to room temperature, and the solution was diluted to volume with deionized water and mixed well This was the Sample Solution. It was analyzed using Atomic Absorption Spectrometer Aanalyst 100. Spectrometer was set up as per Table 3.

TABLE 3

Atomic Absorption Spectrometer Parameters
(Perkin Elmer AAnalyst 100)

| Parameter | Value |
| --- | --- |
| Lamp | Titanium |
| Lamp Current | 40 ma |
| Wavelength | 364.3 nm |
| Slit Width | 0.2 nm |
| Flame Description | Nitrous Oxide-Acetylene |
| Flow ratio for Nitrous Oxide-Acetylene | 4.0:3.5-4.0 tic marks on flowmeters |
| Reading Time | 3.0 sec |
| Replicate Readings | 3 |
| Calibration Curve | Linear |

Blank and standard solutions were prepared as per procedure given below:

Preparation of Standard Solutions

1. Pipette 2 mL, 3 mL, and 5 mL of 1000 μg/mL of titanium standard solution into three separate 100 mL glass volumetric flasks containing about 20 mL of deionized water.
2. Add 10 mL of sulfuric acid and 10 mL of matrix modifier to each flask using dispensers.

Caution! Add sulfuric acid slowly while agitating the flask. Let the flask cool to room temperature. Dilute to volume with deionized water and mix well. The concentration of the standards will be 20 μg/mL, 30 μg/mL, and 50 μg/mL, respectively. The standard solutions should be prepared daily.

Preparation of Blank Solution

Add about 50 mL of deionized water first, then add 20 mL of matrix modifier, and 20 mL of sulfuric acid into a 200 mL glass volumetric flask. Dilute to volume with deionized water and mix well.

Caution! Add sulfuric acid slowly while agitating the flask. Let the flask cool to room temperature. Dilute to volume with deionized water and mix well.

Calculation

The actual reading of the instrument was 30.50 μg/mL and the sample weight was 0.1028 g, the measured concentration of titanium dioxide in the sample was:

$$\% \text{ TiO}_2 = 30.50 \times \frac{100}{0.1028} \times 1.668 \times 10^{-4} = 4.95\%$$

The above written description of the invention provides a manner ard process of making and using it such that any person skilled in this art is enabled to make and use the same, this enablement being provided in particular for the subject matter of the appended claims, which make up a part of the description.

All references, patents, applications, tests, standards, documents, publications, brochures, texts, articles, etc. mentioned herein are incorporated herein by reference. Where a numerical limit or range is stated, all values and subranges therewithin are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

What is claimed is:

1. A method, comprising:
   combining a sample to be analyzed with sulfuric acid, nitric acid, and one or more fluoride salts selected from the group consisting of LiF, NaF and KF, and heating the combination.

2. The method of claim 1, further comprising allowing the sample to cool and analyzing the cooled sample for metal content.

3. The method according to claim 2, wherein aluminum nitrate, sodium chloride, phosphoric acid and water are combined with the cooled sample prior to analysis.

4. The method according to claim 3, wherein said heating is microwave heating.

5. The method according to claim 4, wherein said sample is a cosmetic sample, and wherein said metal includes Ti.

6. The method according to claim 2, wherein said sample is a cosmetic sample, and wherein said metal includes Ti.

7. The method according to claim 1 wherein said heating is microwave heating.

8. A composition, consisting essentially of aluminum nitrate, sodium chloride, phosphoric acid and water.

9. The composition according to claim 8, consisting essentially of 69.0 g aluminum nitrate, 8.5 g sodium chloride, 200 ml % phosphoric acid and 750 ml water.

10. A composition comprising 10.0 ml of sulphuric acid, 1.5 ml of 70% nitric acid, and 0.25 g of one or more fluoride salts selected from the group consisting of LiF, NaF, RbF, CsF and KE.

11. The composition according to claim 10, consisting essentially of 10.0 ml of 95-98% sulphuric acid, 1.5 ml of 70% nitric acid, and 0.25 g of one or more fluoride salts selected from the group consisting of LiF, NaF and KF.

12. The composition according to claim 10, further comprising a sample to be analyzed.

13. The composition according to claim 12, consisting essentially of 10.0 ml of 95-98% sulphuric acid, 1.5 ml of 70% nitric acid, 0.25 g of one or more fluoride salts selected from the group consisting of LiF, NaF and KF, and a sample to be analyzed.

* * * * *